(12) United States Patent
Wagner et al.

(10) Patent No.: US 9,788,872 B2
(45) Date of Patent: Oct. 17, 2017

(54) PERIPROSTHETIC FRACTURE REPAIR

(75) Inventors: Michael Wagner, Vienna (AT); Juerg Leemann, Berne (CH); Christoph Fuerst, Lohn-Ammannsegg (CH); Carole Appenzeller Frieden, Lyss (CH); Martin Altmann, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1301 days.

(21) Appl. No.: 12/740,074

(22) PCT Filed: Nov. 5, 2008

(86) PCT No.: PCT/US2008/082470
§ 371 (c)(1),
(2), (4) Date: Apr. 27, 2010

(87) PCT Pub. No.: WO2009/064643
PCT Pub. Date: May 22, 2009

(65) Prior Publication Data
US 2010/0262194 A1 Oct. 14, 2010

Related U.S. Application Data

(60) Provisional application No. 60/987,560, filed on Nov. 13, 2007.

(51) Int. Cl.
*A61B 17/80* (2006.01)
*A61B 17/17* (2006.01)
(Continued)

(52) U.S. Cl.
CPC .......... *A61B 17/80* (2013.01); *A61B 17/1728* (2013.01); *A61B 17/84* (2013.01); *A61B 17/864* (2013.01); *A61B 17/8685* (2013.01)

(58) Field of Classification Search
USPC ............................................. 606/70, 71, 281
See application file for complete search history.

(56) References Cited

U.S. PATENT DOCUMENTS 3,824,995 A    7/1974  Getscher et al.
4,120,298 A   10/1978  Fixel
(Continued)

FOREIGN PATENT DOCUMENTS

DE    30 06 518    8/1981
EP    0 615 728    9/1994
(Continued)

*Primary Examiner* — Anu Ramana
(74) *Attorney, Agent, or Firm* — Fay Kaplun & Marcin, LLP

(57) ABSTRACT

A device for treating fractures, comprises a plate receiving structure including on a bone facing side thereof a recess sized and shaped to receive a fixation plate anchored in a desired position on a bone and a mating structure sized and located to engage a corresponding structure of the fixation plate to prevent relative movement between the fixation plate and the device in combination with at least one leg projecting laterally away from the recess, a first one of the at least one legs including a first fixation element receiving hole extending therethrough, the first leg being positioned and oriented so that, when the device is received on a fixation plate anchored to the bone in the desired position, the first fixation element receiving hole is aligned to pass a fixation element inserted therethrough into the bone without passing through a longitudinal axis of the medullary canal.

23 Claims, 8 Drawing Sheets

(51) Int. Cl.
*A61B 17/84* (2006.01)
*A61B 17/86* (2006.01)

(56) References Cited

U.S. PATENT DOCUMENTS

| | | | |
|---|---|---|---|
| 4,263,904 | A | 4/1981 | Judet |
| 4,506,662 | A | 3/1985 | Anapliotis |
| 4,565,193 | A | 1/1986 | Streli |
| 4,973,332 | A | 11/1990 | Kummer |
| 5,015,248 | A | 5/1991 | Burstein et al. |
| 5,120,171 | A * | 6/1992 | Lasner .......... 411/308 |
| 5,151,103 | A * | 9/1992 | Tepic et al. .......... 606/291 |
| 5,462,547 | A | 10/1995 | Weigum |
| 5,591,168 | A | 1/1997 | Judet et al. |
| 5,973,223 | A | 10/1999 | Tellman et al. |
| 6,338,734 | B1 | 1/2002 | Burke et al. |
| 6,503,281 | B1 | 1/2003 | Mallory |
| 6,652,530 | B2 | 11/2003 | Ip et al. |
| 6,755,831 | B2 * | 6/2004 | Putnam et al. .......... 606/311 |
| 7,229,444 | B2 | 6/2007 | Boyd |
| 7,306,600 | B2 * | 12/2007 | Roth et al. .......... 606/53 |
| 2004/0030339 | A1 * | 2/2004 | Wack et al. .......... 606/69 |
| 2004/0225291 | A1 | 11/2004 | Schwammberger et al. |
| 2004/0236337 | A1 | 11/2004 | Deloge et al. |
| 2005/0049595 | A1 | 3/2005 | Suh et al. |
| 2005/0101959 | A1 | 5/2005 | Mitkovic |
| 2005/0240187 | A1 | 10/2005 | Huebner et al. |
| 2006/0217722 | A1 | 9/2006 | Dutoit et al. |
| 2008/0103501 | A1 * | 5/2008 | Ralph et al. .......... 606/61 |

FOREIGN PATENT DOCUMENTS

| | | |
|---|---|---|
| EP | 0 934 731 | 8/1999 |
| FR | 1 599 483 | 8/1970 |
| FR | 2 712 173 | 5/1995 |
| GB | 2 331 244 | 5/1999 |
| GR | 1003502 | 4/1999 |
| JP | H02-211141 | 8/1990 |
| JP | 0546460 | 6/1993 |
| JP | H06-505423 | 6/1994 |
| JP | H08-299361 | 11/1996 |
| MD | 2 630 | 12/2004 |
| SU | 1634260 | 3/1991 |
| WO | 2006/097729 | 9/2006 |

* cited by examiner

PERIPROSTHETIC FRACTURE REPAIR

PRIORITY CLAIM

The present application claims priority to the U.S. Provisional Application No. 60/987,560 entitled "Periprosthetic Fracture Repair," filed Nov. 13, 2007. The specification of the above-identified application is incorporated herewith by reference.

BACKGROUND

The use of fixation plates to treat periprosthetic fractures has been limited by the interference of a prosthetic within the medullary canal poses to the insertion of screws, pegs, nails or other fixation devices therethrough.

SUMMARY OF THE INVENTION

The present invention is directed to a device for treating fractures, comprising a plate receiving structure including on a bone facing side thereof a recess sized and shaped to receive a fixation plate and a mating structure sized and located to engage a corresponding structure of the fixation plate to prevent relative movement between the fixation plate and the device in combination with one or more legs projecting laterally away from the recess, at least a first one of the legs including a fixation element receiving hole extending therethrough, the first leg being positioned and oriented so that, when the device is received on a fixation plate anchored to the bone, the fixation element receiving hole is aligned to pass a fixation element inserted therethrough into the bone without passing through a longitudinal axis of the medullary canal. Those skilled in the art will understand that medullary canals are generally neither straight nor concentric with the bone. Thus the axis of the medullary canal, as that term is used in this application, refers to a curve connecting points in the center of the medullary canal along the length of the bone.

The present invention is further directed to a method for treating fractures, comprising coupling a first end of a longitudinal fixation device to a bone on a first side of a fracture so that the longitudinal fixation device extends along the bone substantially parallel to a longitudinal axis of the medullary canal and coupling a first lateral fixation device to a portion of the longitudinal fixation device extending over a portion of the bone on a second side of the fracture by mating the longitudinal fixation device within a recess of the first lateral fixation device in combination with coupling the first lateral fixation device to the bone by inserting a fixation element through a hole formed in a portion thereof separated from the longitudinal fixation device by a selected distance around a portion of a circumference of the bone.

DETAILED DESCRIPTION

Figures 1, 2:
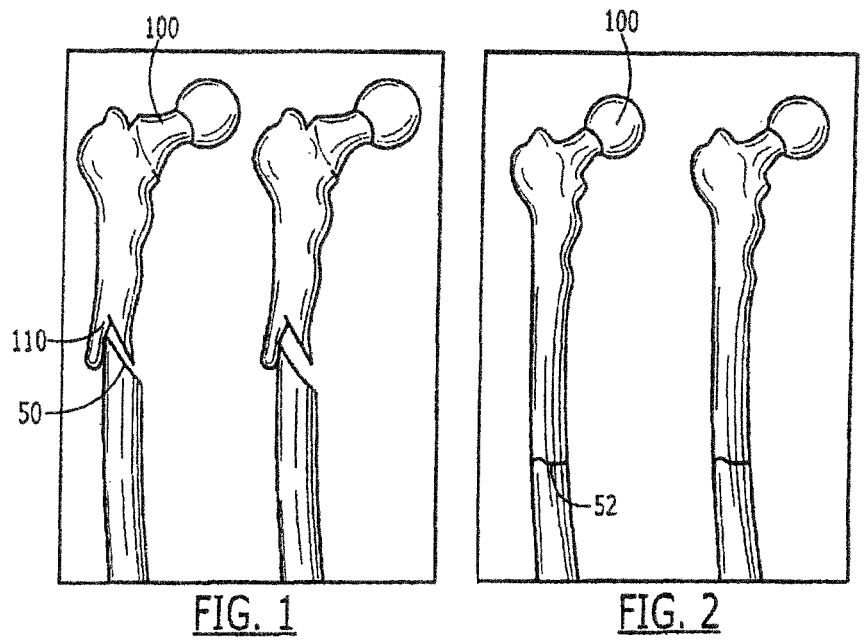
FIG. 1 is a side view of a fracture located on a distal end of a hip prosthesis.
FIG. 2 is a side view of a fracture located distal to a hip prosthesis.

The present invention may be further understood with reference to the following description and to the appended drawings, wherein like elements are referred to with the same reference numerals. The present invention relates to devices for treatment of fractures. In particular, the invention relates to improved methods and systems for repairing periprosthetic fractures. Although exemplary embodiments of the present invention will be discussed with reference to knee and hip prostheses, the present invention may be successfully implemented in any long bone including a prosthetic device inserted into its medullary canal. In addition, as would be understood by those skilled in the art, the present invention may be used for the treatment of fractures around nails and for "conventional" fractures in patients with poor bone quality. The present invention allows the user to apply standard fixation plates while placing screws and/or pins therethrough into the bone along paths selected to: 1) avoid any prosthesis in the medullary canal; 2) align the screws/pins non-parallel to one another to improve purchase in the bone; and/or 3) maximize the length of cancellous bone through which the screws/pins pass.

Periprosthetic fractures may occur intraoperatively (during implantation or replacement of a prosthetic), or postoperatively (e.g., as a result of stress or trauma to the bone in which the prosthetic was previously implanted). As would be understood by those skilled in the art, fractures have been effectively treated by stabilizing the bone using fixation plates (e.g., dynamic compression plates (DCPs), locking compression plates (LCPs), etc.), which typically comprise a metal plate including a plurality of holes through which anchoring of screws or other fixation devices are inserted into underlying bone tissue. Periprosthetic fractures are more difficult to treat than ordinary fractures because a prosthesis extending within the medullary canal may interfere with the proper coupling of a fixation plate across the fracture by preventing the fixation devices from being inserted through the bone across the medullary canal. For example, hip prostheses may interfere with certain fractures of the femur. These hip prostheses often include a ball joint and a stem which is inserted into the medullary canal of the femur. As the femur absorbs significant stresses with each step, to adequately couple a fixation plate thereto, it is desired to maximize the purchase of the fixation devices in the femur.

Figure 3:
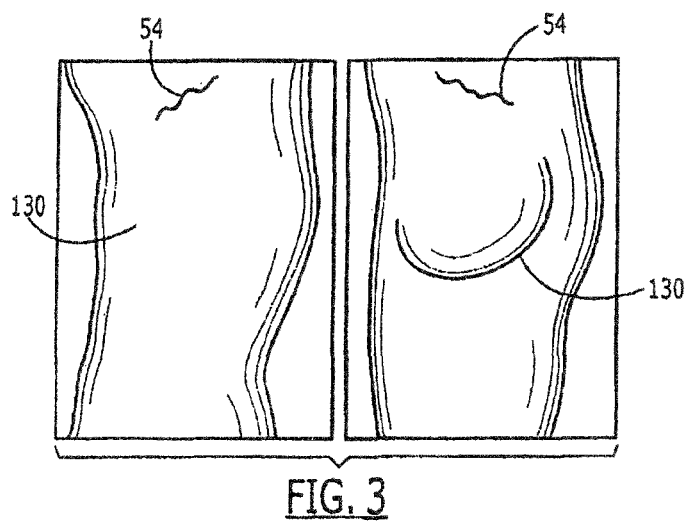
FIG. 3 is a side view of a fracture located near to a knee prosthesis.

In determining a course of treatment, the needs of the patient must be considered. For example, an active 55 year old with a periprosthetic fracture will likely have functional demands different from those of a sedentary 85 year old. Important factors to consider include the location of the fracture, how well-fixed the prosthesis is, and the quality of the femoral bone stock. The Vancouver classification divides periprosthetic hip fractures into three categories: Type A fractures are trochanteric (i.e., disposed at or near the greater or lesser trochanters); Type B fractures occur around the stem of the prosthesis; and Type C fractures occur so far from the stem that the fracture may be treated as a general fracture (i.e., the prosthesis may be ignored). Of these fractures, Type B is the most common. As used in the following descriptions of exemplary embodiments of the invention, the term "distal" refers to a direction away from the end of the bone through which the prosthesis is inserted into the medullary canal. Thus, the distal end of a hip prosthesis is that which is located furthest from the pelvis and the proximal end is that which is nearest to the pelvis. FIG. 1 shows an example of a Type B fracture 50 located along a distal portion 110 of a hip prosthesis 100. As discussed above, the present invention may also be used to treat general fractures (e.g., Type C fractures). An example of a Type C fracture is shown in FIG. 2. In particular, FIG. 2 shows a fracture 52 located distal of the hip prosthetic 100. However, those skilled in the art will understand that the apparatus according to the present invention may also be used to treat Type A fractures as well as similar fractures of other bones. For example, FIG. 3 shows a treatable fracture 54 located near a knee prosthetic 130.

Regardless of how the fracture is classified, complications common to each of the fracture types may make proper treatment critical while creating difficulties, rendering aspects of standard fracture treatment unsuitable. For example, standard fixation plates are typically fixed by inserting one or more fixation devices (e.g., bone screws) substantially diametrically through the bone. Thus, these fixation devices pass through the periosteum and compact bone adjacent to the fixation plate, through the medullary canal and then into the compact bone on the opposite side of the medullary canal. When a prosthesis occupies the medullary canal, inserting a screw directly therethrough is no longer possible and inserting the screw through only that portion of compact bone between the fixation plate and the medullary canal often does not provide sufficient anchorage. Thus, it is desirable to maximize the length of the screw within the compact bone. Accordingly, exemplary embodiments of fracture repair devices according to the present invention, as will be described below, enable the anchoring of screws or other fixation devices along extended paths through compact bone without contacting the prosthesis occupying the medullary canal. Furthermore, the devices and methods according to the present invention may also allow the user to customize the configuration and location of the fixation plate to achieve a desired fracture treatment.

Exemplary embodiments of a fixation kit according to the present invention will now be described with reference to fracture repair devices designed to work in conjunction with any conventional fixation plate such as, for example, locking compression plates (LCPs). Exemplary embodiments of the fracture repair devices may be utilized in conjunction with any number of different types of LCPs or other fixation plates including, for example, an LCP broad curved plate, an LCP broad plate, an LCP Distal Femur (DF) plate, an LCP Less Invasive Stablization System (LISS) plate, an LCP proximal femur plate, an LCP proximal femur with hook plate, an LCP condylar plate, etc. As will be understood by those skilled in the art, the exemplary fracture repair devices may also be used with other conventional fixation plates in addition to LCPs. Thus, the fixation plate may be selected to fit a specific situation in the same manner as would be done if there were no prosthesis or other reason for avoiding the insertion of fixation devices through the axis of the medullary canal.

Figure 4:
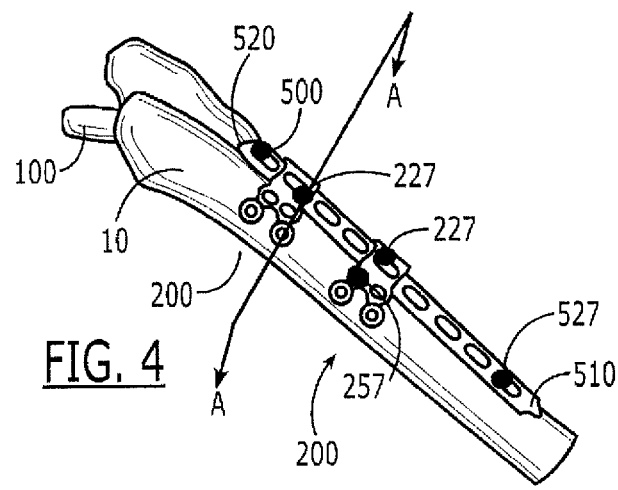
FIG. 4 is a perspective view of an embodiment of a fixation kit according to the invention.
Figure 5:
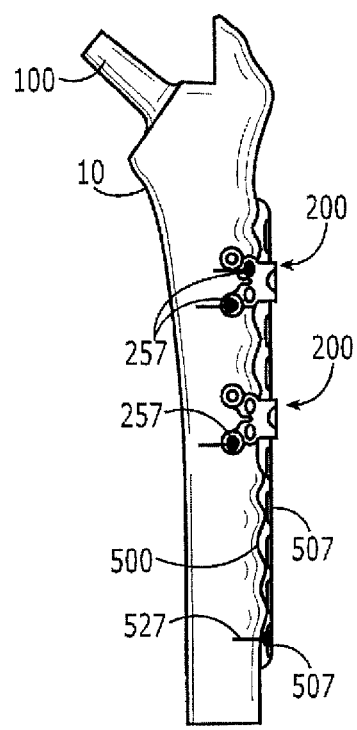
FIG. 5 is a side view of the fixation kit of FIG. 4.
Figure 6:
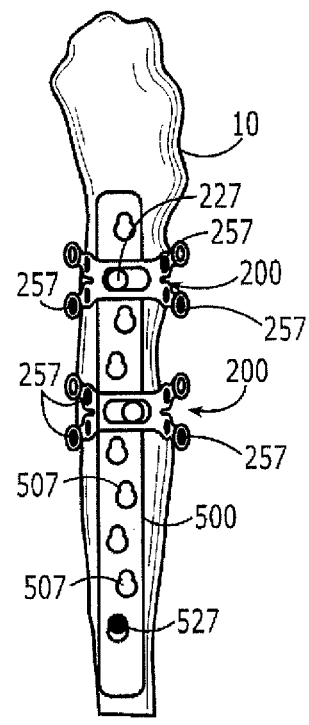
FIG. 6 is a front view of the fixation kit of FIG. 4.

FIGS. 4-6 show a fixation kit including an LCP 500 and two fracture repair devices 200 in place on a femur 10. An intermedullary prosthesis 100 (shown in hidden view) has been inserted into the medullary canal of the femur 10 and the LCP 500 extends proximally from a distal end 510 on a portion of the femur 10 distal of a distal end of the prosthesis 100 across a fracture to a proximal end 520. Two devices 200 are received over proximal and medial portions of the LCP 500 as these portions of the LCP 500 overlay the prosthesis 100. As the distal end 510 extends distally beyond the distal end of the prosthesis 100, it may be secured to the femur in any conventional manner (e.g., by one or more bone screws inserted straight through the medullary canal and the compact bone on either side thereof). As would be understood by those skilled in the art, the size, configuration and/or location of the devices 200 may vary depending on anatomy, fracture location and the position and/or size of a prosthesis relative to the LCP 500. For example, devices 200 may be placed only where the LCP overlays a prosthesis, on both sides of a fracture regardless of location of the fracture relative to the LCP 500 or in any other desired arrangement so long as the required bond between the LCP 500 and the underlying bone is established. Thus, one or more additional devices 200 may be attached to the distal end 510 of the LCP 500 or at any other locations to provide further stabilization. The LCP 500 of FIGS. 4-6 extends distally beyond the distal end of the prosthesis 100. However, in other embodiments a shorter LCP may be selected with devices 200 providing support at all points along the length thereof. Those skilled in the art will understand that the number and the location of the devices 200 may be determined according to physician preference. Therefore, in some embodiments the LCP 500 may be coupled to only a single device 200 (e.g., by centering the device 200 over the fracture) supplemented as desired by additional fixation devices including, for example, screws inserted only through the portion of compact bone adjacent to the LCP 500. Each device 200 is coupled to the LCP 500 via a screw 227 and includes one or more screws 257 or other fixation devices that anchor the device 200 to the bone 10.

As shown in FIG. 5, a distal portion of the LCP 500 extends beyond the prosthesis 100 and is anchored directly into the bone through the medullary canal as is done in the manner of general fractures, when no prosthesis is present. The distal portion may be anchored using any number of screws 527 spaced in accordance with physician preference. Portions of the LCP 500 that extend along the length of the prosthesis 100 either contain no screws that enter the medullary canal (e.g., portions not coupled to a device 200) or are secured via a device 200, which is screwed (via the screws 257) at an angle into the bone 10 to avoid the prosthesis 100.

Figure 7:
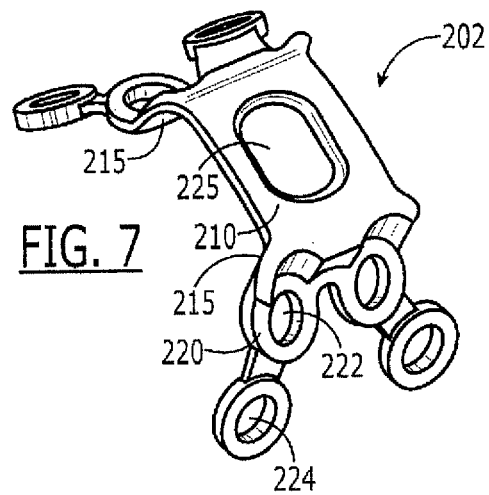
FIG. 7 is a perspective view of a first embodiment of an attachment plate according to the invention.
Figure 8:
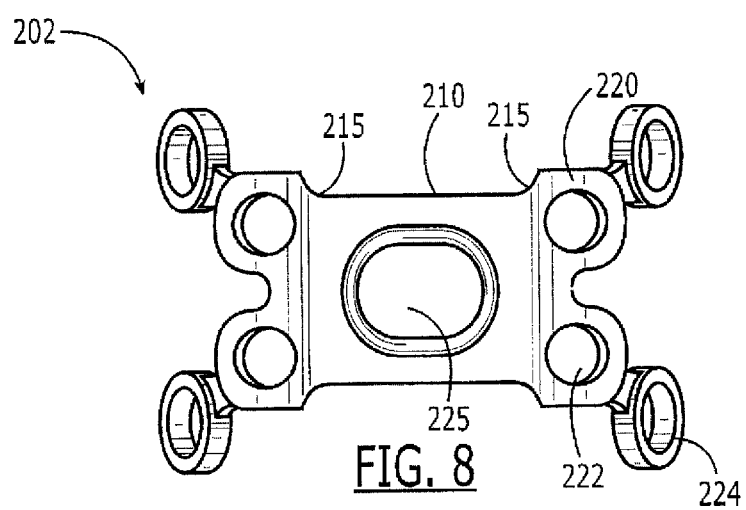
FIG. 8 is a top view of the attachment plate of FIG. 7.
Figure 9:
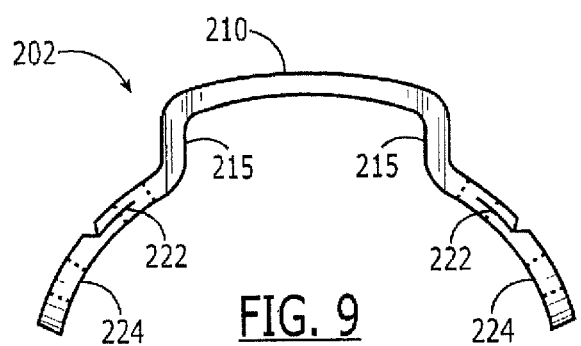
FIG. 9 is a front view of the attachment plate of FIG. 7.

The device 200 shown in FIGS. 7-9 is shaped for use in conjunction with the LCP 500 of FIGS. 4-6. Of course, those skilled in the art will understand that any number of varieties of devices 200 may be formed for use in conjunction with any of a variety of different fixation plates of different sizes and shapes. The device 200 includes a locking attachment plate 202 formed of a substantially rigid biocompatible material such as, for example, plastic, medical-grade steel or titanium as would be understood by those skilled in the art. The attachment plate 202 includes a body 210 including, on a bone-facing side thereof, a recess contoured to receive the LCP 500. Sidewalls 215 of the recess may preferably be shaped to substantially conform to the contours of the LCP 500. Although the sidewalls 215 need not form a tight fit against corresponding sides of the LCP 500, some embodiments may include sidewalls that snap-fit or otherwise couple to the LCP 500. The body 210 may also include a coupling feature that corresponds to a corresponding feature on the LCP 500. For example, the body 210 may include a centrally located screw hole 225 that corresponds to a coupling arrangement (e.g., a threaded bore) of the LCP 500. Thus, the body 210 may be coupled to the LCP 500 by aligning the attachment plate 202 over to the LCP 500 and inserting a screw (e.g., the screw 227) or other fixation device through the hole 225 and into the threaded bore. The bore may pass through the entire body of the LCP 500, enabling the screw 227 to extend past a bone-facing surface of the LCP 500. Thus, in some embodiments, the screw 227 may be driven into the compact bone on the side of the medullary canal facing the LCP 500 without contacting the underlying intermedullary prosthesis. However, in other embodiments, the screw 227 may not extend past the LCP 500, serving only to couple the LCP 500 and the device 200. Alternatively, as would be understood by those skilled in the art, a fracture repair device according to the invention may include a projection aligned to mate with a corresponding recess in an LCP (e.g., the threaded bore), a recess aligned to mate with a corresponding projection of an LCP or a combination of such recess/projection matings. As discussed above, the sidewalls 215 may be snap-fit onto the LCP 500. Other coupling arrangements, such as, for example, friction-fitting, adhesives, bolts, etc. may also be used to couple the LCP 500 and the attachment plate 202 as would be understood by those skilled in the art.

The attachment plate 202 includes one or more arms 220 extending laterally from the sidewalls 215, away from the body 210. Each of the sidewalls 215 includes an arm 220 extending from each end thereof and each of the arms 220 includes a first and a second screw hole 222, 224, respectively, extending therethrough. However, those skilled in the art will understand that the number of arms per sidewall may vary. The arms 220 may be formed integrally with the body 210 or attached separately. Each of the arms 220 is preferably oriented such that a bone-facing surface of the arm 220 is generally follows the contours of a bone on which the arm 220 is to be mounted. Optionally, the arms may be formed of a material which may be bent by a user into a desired configuration to customize the arms 220 to the anatomy of each patient. As shown in FIG. 9, when viewed in a plane substantially perpendicular to a longitudinal axis of the medullary canal, each of the arms 220 extends along a curve substantially approximating the shape of an outer surface of a bone on which it is to be mounted.

As seen in FIGS. 7-9, each arm 220 also extends away from the corresponding side wall 215 at an angle within a plane of the body 210. Those skilled in the art will understand that the selection of this angle and any change in this angle between the first and second screw holes 222, 224 allow for the application of additional screws at different angles and/or at different locations or, for example, to increase the area over which the attachment forces are applied to the bone. As indicated above, each of the arms 220 includes a first screw hole 222 adjacent to the corresponding side wall 215 and a second screw hole 224 extending laterally away from the first screw hole 222. Although each of the arms 220 is shown extending at substantially the same angle, those skilled in the art will understand that the arms 220 may extend at different angles to accommodate varying bone structure, LCP shapes, etc. and may include the same number or different numbers of screw holes.

As described above and as shown in FIG. 9, the arms 220 preferably curve to enable the arms 220 to wrap around the bone 10 in a substantially conforming manner. A degree to which the arms 220 encircle the bone 10 may vary depending on the curvature and the angle of each arm 220 in relation to bone physiology. Thus, the arms 220 may produce a tighter fit when mounted to wide portions of the bone 10, while providing a looser fit when mounted to narrow bone portions. In addition, the arms 220 may flex, allowing the arms 220 to be mounted closer to the bone 10.

Figure 10:
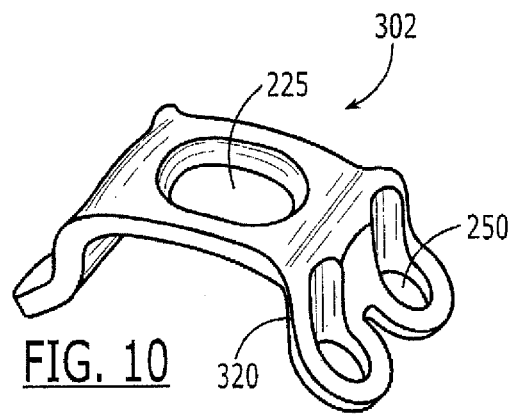
FIG. 10 is a perspective view of a second embodiment of an attachment plate according to the invention.

Each of the first and second screw holes 222, 224, respectively, may be threaded to match a threading of a locking head of a screw 257 or may be otherwise suited to receive the particular fixation device to be employed with the device 200. As would be understood by those skilled in the art, the number of screw holes in each arm 220 may vary based on factors such as LCP shape, bone anatomy, desired degree of stabilization, etc. As shown in FIG. 10, an exemplary attachment plate 302 is substantially similar to the plate 202 of FIGS. 7-9 except that each of the arms 320 has only one screw hole 250 extending therethrough. It will be understood by those of skill in the art that the attachment plate 302 may be used according to the device 200 in substantially the same manner as the attachment plate 202. In some embodiments, one or more arms may not include any holes at all or may contain more than two screw holes.

Each of the holes 250 defines an angle of insertion for the screw 257 selected so that when the attachment plate 202 is mounted onto the bone 10, the screw 257 passes through the bone 10 without diametrically passing through the medullary canal, thereby avoiding contact with the prosthesis 100. Those skilled in the art will understand that the angle is preferably selected to maximize the length of the screw 257 received in the bone 10. Those skilled in the art will also understand that some or all of the screw holes for any of the attachment plates according to the invention may be variable angle locking holes allowing for locking screws to be inserted therethrough and locked to the plate at multiple angles relative to the attachment plate. For example, any or all of the screw holes 222, 224 and 250 may be formed substantially in accord with the description in U.S. Patent Application Publication No. 2005/0165400 filed by Fernandez, Jul. 28, 2005, the entire disclosure of which is hereby incorporated by reference in its entirety.

For example, the screws may have a head shaped like a sphere and threaded with a substantially constant pitch substantially equal to a pitch of a threaded shank of the screw. In addition, an insertion/extraction hole may be cut in the head for the connection of an insertion/extraction tool. The thread cut in the screw head may have a double entry maintaining substantially the same pitch as that of the thread of the shank. Of course, as would be understood by those skilled in the art, the thread profile may vary according to the requirements and according to the mechanical properties of the material of which the screw is formed.

This allows the screw to be inserted into a properly designed screw hole at any angle within a wide range without affecting the position of the thread of the screw head with respect to walls of the screw hole.

Specifically, such a screw hole may be formed in a spherical shape, with edges thereof at both ends of the hole removed in a frusto-conical shape. That is, the screw hole may include two frusto-conical portions extending toward one another from opposite surfaces of the plate and connected at tips of the cones through a partial sphere. The inner wall of each screw hole has a small number of isolated protrusions such as pegs or spikes (e.g., between two and thirty) designed to lock against the threaded spherical head of the screws when the screws are driven in through the screw holes. The protrusions may, for example, be somewhat flattened with a width bigger than its length.

Once such a screw has been driven into such a screw hole, the spherical shape of the screw head allows it to lock against the protrusions without regard to whether the screw extends perpendicular or at a tilt relative to an axis of the screw hole. The angle at which of the screw is locked may then be varied by as much as 20° relative to the axis of the screw hole.

In use, a physician may begin treatment by selecting an LCP 500 of appropriate size and shape, taking into account the width of the bone 10, the location of the fracture and other factors as would be understood by those skilled in the art. The LCP 500 is then aligned over the bone 10 to extend across the fracture in a position selected to stabilize the portions of the bone on both sides thereof. The physician then has the option of initially securing the distal portion of the LCP 500 to the portion of the bone not including a prosthesis within the medullary canal or of selecting one or more attachment plates 202 to achieve the desired coupling of the LCP 500 and the proximal portion of the bone. If securing of the distal portion first is desired, the physician drives the screws 527 directly into the bone 10 in the same manner as would be used for a fracture where no prosthesis was present. Thereafter, the physician may slide the selected plate 202 over the proximal portion of the LCP 500 to the desired alignment and attach the plate 202 to the LCP 500. Alternatively, as would be understood by those skilled in the art, the physician may attach the attachment plate to the bone in a desired location before attaching the LCP 500 to either the plate 202 or any portion of the bone and then slide the LCP 500 through the recess into place between the bone 10 and the attachment plate 202.

The physician may choose to couple the attachment plate 202 to the LCP 500 before attaching the attachment plate 202 to the bone 10. The attachment plate 202 is positioned over a desired location of the LCP 500. As shown in FIGS. 5 and 6, the LCP 500 includes multiple attachment arrangements comprising attachment sites 507 located along the entire length thereof. The attachment sites 507 are spaced apart, either uniformly or at different distances. For example, certain lengths of the LCP 500 may include more attachment sites (i.e., tighter spacing) than others. The attachment sites 507 may correspond to anchoring locations of the screws 227. That is, the attachment arrangements may be the same as the holes through which the screws 527 may be driven although, as would be understood, the screws are used to couple the attachment plate 202 to the LCP 500 will be shorter than those used to directly couple the LCP 500 to the bone so as to avoid interference with the intermedullary prosthesis.

After positioning over the LCP 500 substantially flush with the bone 10, the attachment plate 202 is coupled to the LCP 500 by either driving the screw 227 to a depth beyond the bone-facing surface of the LCP 500 (i.e., into the bone 10) or to a depth within the body of the LCP 500. As an alternative to coupling the attachment plate 202 during treatment, the coupling may occur prior to introduction of the LCP 500 into the patient. The attachment plate 202 is then anchored to the bone 10 by individually driving each screw 257 into the bone 10 at an angle selected by the physician (e.g., to maximize a length of the path the screw travels through the compact bone without entering the medullary canal). The bone 10 beneath each hole 250 is drilled out to a desired depth (e.g., a maximum depth of penetration of the compact bone without contacting the prosthesis 100). As an alternative to drilling, the screws 257 may be self-tapping. As would be understood by those skilled in the art, the maximum depth to which the screws 257 may be driven is a function of known factors such as, for example, bone anatomy and the available insertion angles.

Figure 12:
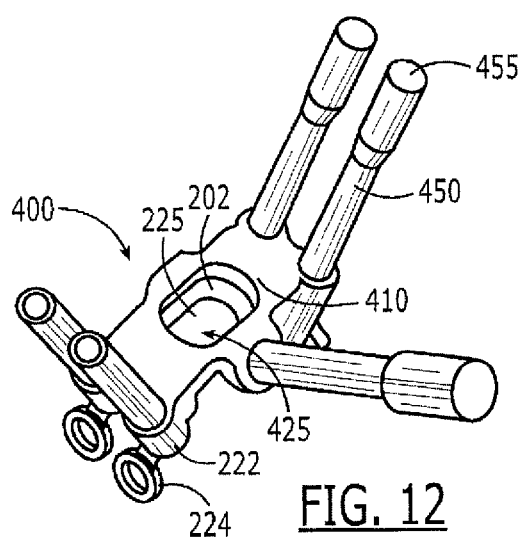
FIG. 12 is a perspective view of an embodiment of an aiming block according to the invention.

As would be understood by those skilled in the art, an aiming device such as an aiming block may be used to facilitate accurate drilling of the bone 10. FIG. 12 shows an exemplary embodiment of an aiming block 400 in an operative position. The aiming block 400, which may be placed over the attachment plate 202 or over the combined attachment plate-LCP, includes a body portion 410 including a hole 425 matching the hole 225. Although the hole 425 is not strictly required, including the hole 425 facilitates visual confirmation that the aiming block 400 has been placed correctly over the attachment plate 202. Once the attachment plate 202 has been positioned at a desired location, the aiming block 400 is placed on top of the attachment plate 202 and aligned therewith. The aiming block 400 includes one or more shafts 450 corresponding to the first hole 222 and/or the second hole 224. The shafts 450 are positioned at desired angles to form a drilling template. A plurality of aiming blocks 400 with different shaft configurations may be available for use, enabling the drilled holes to be oriented at any desired angle. A drilling tool is inserted through a hole 455 located at one end of the shaft 450 and guided through an opening at the opposite end of the shaft 450 into either of the first hole 222 and the second hole 224 and, subsequently, into the bone 10. After reaching the desired drilling depth, the drilling tool is withdrawn from the shaft and additional holes may be created by inserting the drilling tool into further shafts 450. When all the holes have been drilled, the aiming block 400 is removed and the operating site is cleared of bone debris before inserting the screws 257.

Figure 11:
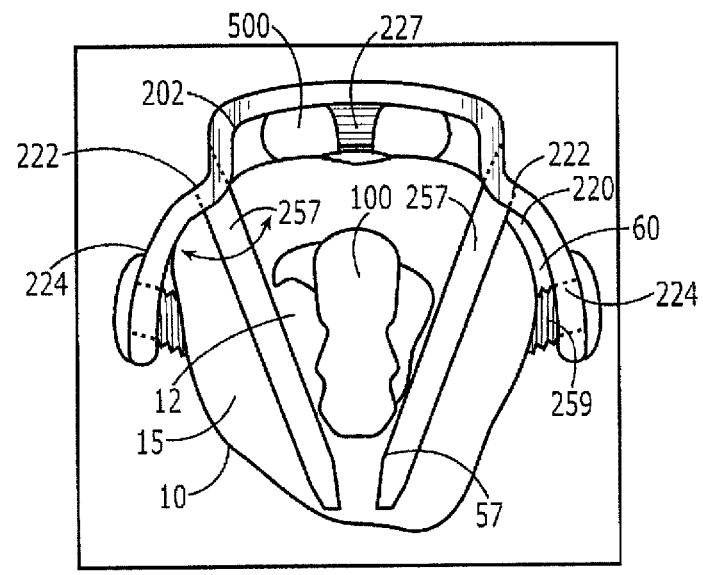
FIG. 11 is cross-sectional view of the fixation kit of FIG. 4.

The screws 257 may then be inserted directly into the first and/or the second holes 222, 224 or guided through the shafts 450 of the aiming block 400. As shown in the cross-sectional view of the fixation kit in FIG. 11, taken along line A-A, a substantial portion of each screw 257 occupies the bone cortex 15 without interfering with a prosthesis 100 within the medullary canal 12. Screws of varying length may be provided as part of the fixation kit to take advantage of the maximum allowable insertion depth. Thus, the screws may be selected to extend from one side of the bone 10 to an opposing side. As seen in FIG. 11, the screws 257 may also occupy a portion of a medullary canal 12 without passing diametrically therethrough or contacting the prosthesis 100. As the screws 257 travel toward their resting positions, the arms 220 may be drawn toward the bone 10 by pressure exerted by head portions of the screws 257. Although a close fit is desired for stability, it may also be desirable not to excessively constrict the bone 10 or the blood supply thereto by drawing the arms 220 too tightly thereagainst. Thus, a small gap 60 may be left between the arms 220 and the bone 10. The gap 60 promotes blood flow and reduces the amount of bone compressed by the attachment plate 202. The gap 60 may be achieved by forming the arms 220 with sufficient curvature such that a bone-facing surface of the arms 220 is substantially concave. The gap 60 may also be a function of the extent to which the screws 257 are driven into the bone 10. If a smaller gap is desired, more of the screw 257 can be driven in. Similarly, less driving will result in a larger gap. Thus, the length of a shaft portion 259 of each screw 257 that is exposed within the gap 60 is variable. Some screws 257 may be driven entirely into the bone 10 while other screws 257 may form large gaps.

Figure 13A:
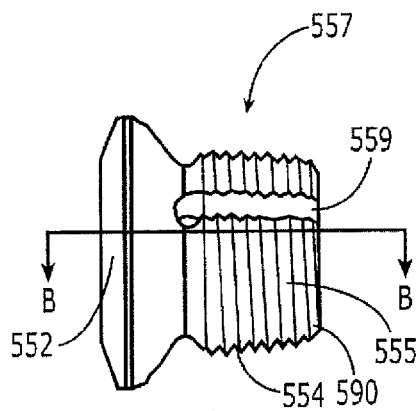
FIG. 13A is a side view of an embodiment of a fixation device according to the invention.
Figure 13B:
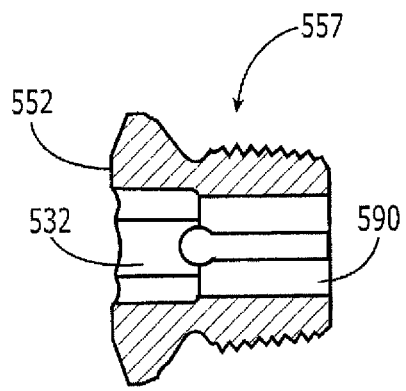
FIG. 13B is a cross-sectional view of the fixation device of FIG. 13A.
Figure 13C:
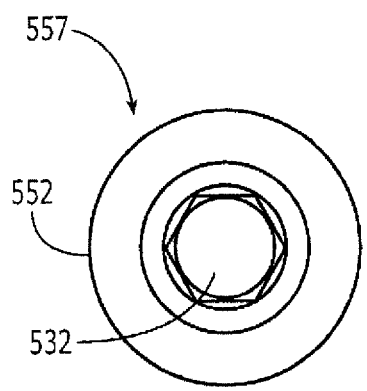
FIG. 13C is a top view of the fixation device of FIG. 13A.
Figure 13D:
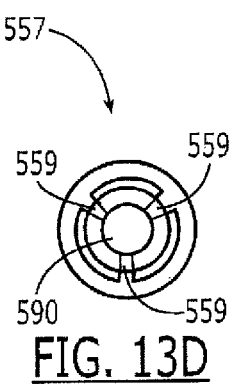
FIG. 13D is a front view of a distal portion of the fixation device of FIG. 13A.

Exemplary embodiments of fixation devices that may be used in conjunction with the device 200 will now be described. FIGS. 13A-13D show an exemplary embodiment of a screw 557 according to the present invention. As shown in the side view of FIG. 13A, the screw 557 includes a conical body comprising a head 552 and a shaft 554 including a plurality of threads 555. The shaft 554 also includes one or more slots 559 extending substantially the entire length thereof. The conical body of the screw 557 tapers from the head 552 toward the shaft 554. FIG. 13B shows a cross-section of the screw 557, taken along line B-B. As shown, a portion of the head 552 includes a recess 532. In the exemplary embodiment, the recess 532 is hex-shaped. The shape of the recess 532 is shown more clearly in the top view of the head 552 illustrated in FIG. 13C. Although the exemplary embodiment utilizes a hex-shaped recess, other shapes (e.g., stars or triangles) may be utilized in other embodiments. FIG. 13D shows a front view of a distal tip 590 of the screw 557. As shown in FIG. 13D, the slots 559 are equidistantly spaced about the perimeter of the distal tip 590. As would be understood by those skilled in the art, the screws may be formed of stainless steel, titanium or a suitable biocompatible polymer.

Figure 14A:
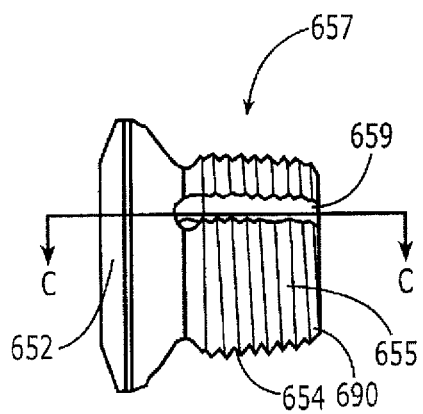
FIG. 14A is a side view of a second embodiment of a fixation device according to the invention.
Figure 14B:
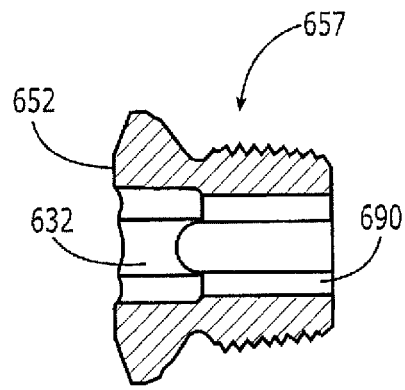
FIG. 14B is a cross-sectional view of the fixation device of FIG. 14A.
Figure 14C:
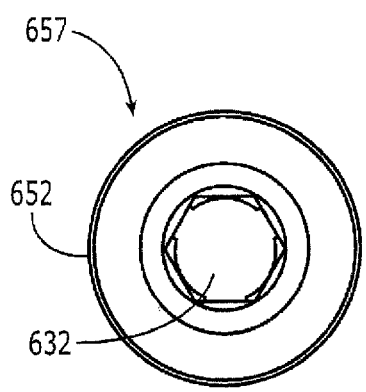
FIG. 14C is a top view of the fixation device of FIG. 14A.
Figure 14D:
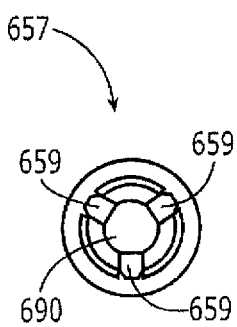
FIG. 14D is a front view of a distal portion of the fixation device of FIG. 14A.

FIGS. 14A-14D show an exemplary embodiment of a screw 657 according to the present invention. The screw 657 includes a cylindrical body comprising a head 652 and a shaft 654 including a plurality of threads 655. The shaft 654 also includes one or more slots 659 extending substantially the entire length thereof. FIG. 14B shows a cross-section of the screw 657. A portion of the head 652 includes a recess 632. As shown in the top view of the head 652 illustrated in FIG. 13C, the recess 632 is hex-shaped. However, other shapes are also possible. FIG. 14D shows a front view of a distal tip 690 of the screw 657. As shown in FIG. 13D, the slots 659 are equidistantly spaced about the perimeter of the distal tip 690.

Figure 15A:
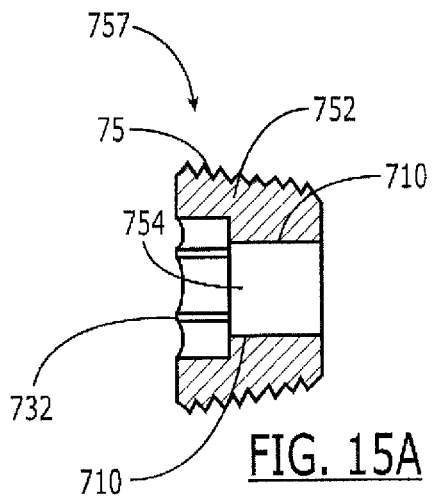
FIG. 15A is a cross-sectional view of a third embodiment of a fixation device according to the invention.
Figure 15B:
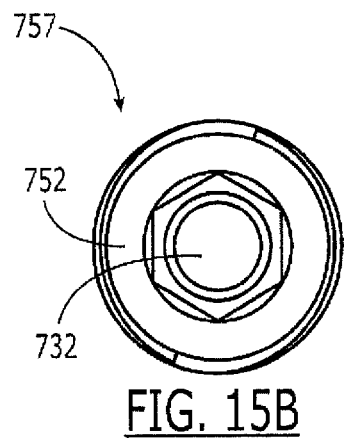
FIG. 15B is a top view of the fixation device of FIG. 15A.

FIGS. 15A and 15B show an exemplary embodiment of a screw 757 according to the present invention. The screw 757 includes an outer member 752 and an inner member 754 that couples to the outer member 752. The inner member 754 extends substantially the entire length of the outer member 752 and includes a hex-shaped recess 732. An inner wall 710 of the outer member 752 defines an interface shaped to mate with the inner member 754 using friction-fitting. However, the inner member 754 may be coupled to the outer member 752 in any number of ways including, for example, screwing in a direction opposite to that of threads 75 running along an outer surface of the outer member 752.

Figure 16A:
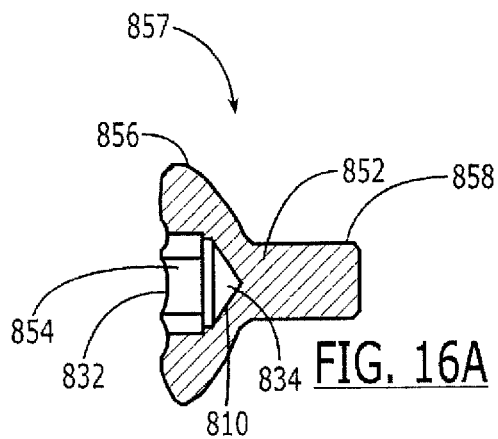
FIG. 16A is a cross-sectional view of a fourth embodiment of a fixation device according to the invention.
Figure 16B:
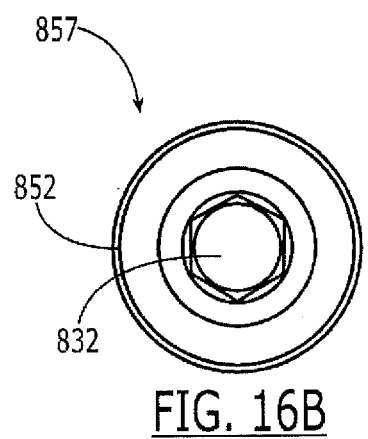
FIG. 16B is a top view of the fixation device of FIG. 16A.

FIGS. 16A and 16B show an exemplary embodiment of a peg 857 according to the present invention. The peg 857 includes an outer member 852 and an inner member 854 that couples to the outer member 852. The inner member 854 extends substantially the entire length of a head portion 856 of the outer member 852 and includes a hex-shaped recess 832. A distal end 834 of the inner member 854 is shaped to conform to the contours of the head 856. An inner wall 810 of the outer member 852 defines an interface shaped to mate with the inner member 854 using friction-fitting. However, the inner member 854 may be coupled to the outer member 852 in any number of ways including, for example, screwing.

Figure 17A:
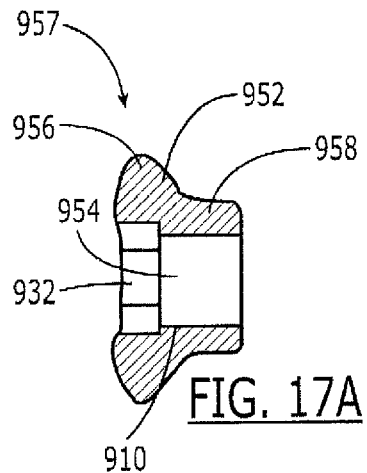
FIG. 17A is a cross-sectional view of a fifth embodiment of a fixation device according to the invention.
Figure 17B:
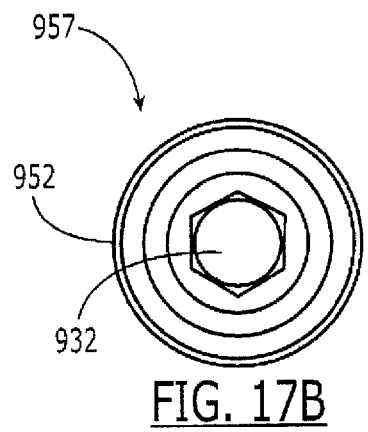
FIG. 17B is a top view of the fixation device of FIG. 17A.

FIGS. 17A and 17B show an exemplary embodiment of a peg 957 according to the present invention. The peg 957 includes an outer member 952 and an inner member 954 that couples to the outer member 952. The inner member 954 extends substantially the entire length of the outer member 952 and includes a hex-shaped recess 932. The outer member 952 includes a head portion 956 and a shaft portion 958 having a diameter less than that of the head 956. An inner wall 910 of the outer member 952 defines an interface shaped to mate with the inner member 954 using friction-fitting. However, the inner member 954 may be coupled to the outer member 952 in any number of ways including, for example, screwing.

Figure 18A:
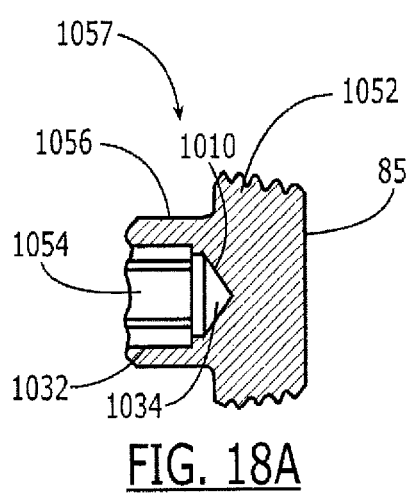
FIG. 18A is a cross-sectional view of a sixth embodiment of a fixation device according to the invention.
Figure 18B:
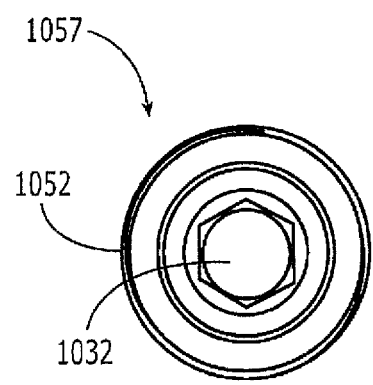
FIG. 18B is a top view of the fixation device of FIG. 18A.

FIGS. 18A and 18B show an exemplary embodiment of a screw 1057 according to the present invention. The screw 1057 includes an outer member 1052 and an inner member 1054 that couples to the outer member 1052. The inner member 1054 extends substantially the entire length of a head portion 1056 of the outer member 1052 and includes a hex-shaped recess 1032. The outer member 1052 includes a head portion 1056 and a shaft portion 1058 having a diameter greater than that of the head 1056. A distal end 1034 of the inner member 1054 is conically shaped. An inner wall 1010 of the outer member 1052 defines an interface shaped to mate with the inner member 1054 using friction-fitting. However, the inner member 1054 may be coupled to the outer member 1052 in any number of ways including, for example, screwing in a direction opposite to that of threads 85 running along an outer surface of the outer member 1052.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A device for treating fractures, comprising:
 a plate receiving structure including on a bone facing side thereof a recess sized and shaped to receive a fixation plate anchored in a desired position on a long bone;
 a mating structure sized and located to engage a corresponding structure of the fixation plate to prevent relative movement between the fixation plate and the plate receiving structure; and
 a first leg projecting laterally away from the recess, the first leg including a first fixation element receiving hole extending therethrough along a first hole axis, the first leg being positioned and oriented so that, when the device is received on a fixation plate anchored to the long bone in the desired position, the first hole axis is aligned to pass a fixation element inserted through the first hole through the long bone from a first side of the long bone beyond a medullary canal of the long bone toward a second side of the long bone opposite the first side without passing through the medullary canal.

2. The device according to claim 1, further comprising a second leg including a second fixation element receiving hole extending therethrough along a second hole axis oriented so that when the device is received on a fixation plate anchored to the bone in the desired position, the second hole axis is aligned to pass a fixation element inserted through the second hole through the long bone from the first side beyond the medullary canal toward the second side without passing through the medullary canal.

3. The device according to claim 1, wherein the device includes four legs and wherein each of the four legs includes first and second fixation element receiving holes.

4. The device according to claim 1, wherein the device includes side walls joined to one another by a central body, the side walls being oriented so that, when received on a bone in a desired position, the side walls extend substantially radially outward from the bone with inner surfaces of the side walls and a bone facing side of the central body defining the recess.

5. The device according to claim 4, wherein the mating structure is formed on the central body.

6. The device according to claim 5, wherein the mating structure comprises a fixation element receiving hole positioned so that when a fixation device is received in the recess, the fixation element receiving hole of the mating structure aligns with a fixation element receiving hole of the fixation plate.

7. The device according to claim 6, wherein the mating structure comprises a projection extending from the bone facing side of the central body, the projection being positioned so that when a fixation plate is received in the recess, the projection aligns with a fixation element receiving hole of the fixation plate.

8. The device according to claim 1, wherein the recess is sized to form a snap fit with a fixation plate inserted thereinto.

9. The device according to claim 1, wherein the fixation element receiving holes are variable angle locking holes.

10. The device according to claim 1, wherein the legs are formed so that, when a fixation plate is received in the recess, bone facing surfaces of the legs rest substantially flush on a surface of the bone.

11. The device according to claim 1, wherein bone facing surfaces of the legs are curved in a manner substantially mirroring an outer surface of a bone on which the device is to be received.

12. A method for treating fractures, comprising:
coupling a first end of a longitudinal fixation device to a long bone on a first side of a fracture so that the longitudinal fixation device extends along the long bone substantially parallel to a longitudinal axis of the medullary canal;
coupling a first lateral fixation device to a portion of the longitudinal fixation device extending over a portion of the long bone on a second side of the fracture by mating the longitudinal fixation device within a recess of the first lateral fixation device; and
coupling the first lateral fixation device to the long bone by inserting a fixation element through a hole formed in a portion thereof separated from the longitudinal fixation device by a selected distance around a portion of a circumference of the long bone, the fixation element being inserted into the hole along a hole axis such that the fixation element extends from a first side of the long bone beyond a medullary canal of the long bone toward a second side of the long bone opposite the first side while avoiding a medullary canal of the long bone.

13. The method according to claim 12, wherein the first lateral fixation device includes a plurality of legs projecting away from the recess in a direction substantially perpendicular to the longitudinal axis of the medullary canal, at least first and second ones of the legs including lateral fixation element receiving holes extending therethrough.

14. The method according to claim 13, wherein each of the legs of the first lateral fixation device includes a fixation element receiving hole.

15. The method according to claim 13, wherein the bone includes an intermedullary prosthesis received in a medullary canal thereof, further comprising inserting through the lateral fixation element receiving holes one of pegs and screws along paths selected to avoid interference with the intermedullary prosthesis.

16. The method according to claim 12, wherein the first end of the longitudinal fixation device is fixed to the bone by a fixation element inserted therethrough to pass substantially diametrically through the intermedullary canal.

17. The method according to claim 12, wherein the first end of the longitudinal fixation device is fixed to the bone by a second lateral fixation device receiving the first end of the longitudinal fixation device in a recess thereof.

18. The method according to claim 12, wherein the first lateral fixation device includes side walls joined to one another by a central body, the side walls extending substantially radially outward from the bone with inner surfaces of the side walls and a bone facing side of the central body defining the recess.

19. The method according to claim 18, wherein the first lateral fixation device includes a projection extending from a bone facing side of a central body extending between the side walls, the projection being positioned so that when a fixation plate is received in the recess, the projection aligns with a fixation element receiving hole of the longitudinal fixation device.

20. The method according to claim 12, further comprising fixing the first lateral fixation device to the longitudinal fixation device by aligning a mating structure of the first lateral fixation device with a corresponding structure of the longitudinal fixation device.

21. The method according to claim 20, wherein the mating structure includes a fixation element receiving hole and wherein the corresponding structure on the longitudinal fixation device includes a fixation element receiving hole.

22. A kit for treating fractures, comprising:
a lateral fixation device comprising:
a longitudinal fixation device receiving structure including on a long bone facing side thereof a recess sized and shaped to receive a fixation plate which, when anchored in a desired position on the long bone, extends substantially parallel to a longitudinal axis of the medullary canal of the long bone;
a mating structure sized and located to engage a corresponding structure of the fixation plate to prevent relative movement between the fixation plate and the device; and
a first leg projecting laterally away from the recess, the first leg including a first fixation element receiving hole extending therethrough, a first hole axis of the first fixation element receiving hole is aligned to pass a fixation element inserted through the first hole through the long bone from a first side of the long bone beyond a medullary canal toward a second side of the long bone opposite the first side without passing through the medullary canal; and instructions for performing the following steps:

coupling a first end of a longitudinal fixation device to the long bone on a first side of a fracture so that the longitudinal fixation device extends along the long bone substantially parallel to a longitudinal axis of the medullary canal of the long bone;

coupling the lateral fixation device to a portion of the longitudinal fixation device extending over a portion of the long bone on a second side of the fracture by mating the longitudinal fixation device within the recess of the lateral fixation device; and coupling the lateral fixation device to the bone by inserting a fixation element through the first fixation hole formed in a portion thereof separated from the longitudinal fixation device by a selected distance around a portion of a circumference of the bone, the fixation element being inserted along the first hole axis through the lateral fixation device and the long bone from the first side toward the second side while avoiding the medullary canal.

23. A device for treating fractures, comprising:

a plate receiving structure including on a bone facing side thereof a recess sized and shaped to receive a fixation plate anchored in a desired position on a long bone;

a mating structure sized and located to engage a corresponding structure of the fixation plate to prevent relative movement between the fixation plate and the plate receiving structure; and a first leg projecting laterally away from the recess, the first leg including a first fixation element receiving hole extending therethrough along a first hole axis, the first leg being positioned and oriented so that, when the device is received on a fixation plate anchored to the long bone in the desired position, the first hole axis is aligned to pass a fixation element inserted through the first hole through the long bone from a first side of the long bone beyond a medullary canal of the long bone toward a second side of the long bone opposite the first side without passing through a longitudinal axis of the medullary canal.

\* \* \* \* \*